US010064716B2

(12) United States Patent
Norton

(10) Patent No.: US 10,064,716 B2
(45) Date of Patent: Sep. 4, 2018

(54) ADJUSTABLE LOOP CONSTRUCTS AND TECHNIQUES

(71) Applicant: Biomet Sports Medicine, LLC, Warsaw, IN (US)

(72) Inventor: Daniel Norton, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 506 days.

(21) Appl. No.: 14/081,209

(22) Filed: Nov. 15, 2013

(65) Prior Publication Data

US 2015/0141995 A1    May 21, 2015

(51) Int. Cl.
| | |
|---|---|
| *A61B 17/12* | (2006.01) |
| *A61F 2/08* | (2006.01) |
| *A61B 17/82* | (2006.01) |
| *A61B 17/06* | (2006.01) |
| *A61B 17/84* | (2006.01) |
| *A61B 17/04* | (2006.01) |

(52) U.S. Cl.
CPC ........ *A61F 2/0811* (2013.01); *A61B 17/0401* (2013.01); *A61B 17/06166* (2013.01); *A61B 17/823* (2013.01); *A61B 17/842* (2013.01); *A61B 2017/0414* (2013.01); *A61B 2017/0417* (2013.01); *A61B 2017/0459* (2013.01); *A61B 2017/0462* (2013.01); *A61B 2017/06185* (2013.01); *A61F 2002/0852* (2013.01); *A61F 2002/0882* (2013.01)

(58) Field of Classification Search
CPC ............ A61F 2/0811; A61F 2002/0852; A61F 2002/0882; A61B 17/0401; A61B 17/06166; A61B 17/823; A61B 17/842; A61B 2017/0414; A61B 2017/0417; A61B 2017/06185; A61B 17/0485; A61B 2017/0459; A61B 2017/0462; A61B 2017/0477; A61B 2017/0475; A61B 2017/06019; A61B 2017/0496
USPC ......... 606/232–233, 300–331, 74; 623/13.14
See application file for complete search history.

(56) References Cited

U.S. PATENT DOCUMENTS

| | | | | |
|---|---|---|---|---|
| 4,319,428 | A * | 3/1982 | Fox ........................ | A01G 17/04 24/115 H |
| 5,062,344 | A * | 11/1991 | Gerker ................... | D07B 1/185 289/1.5 |
| 6,527,795 | B1 * | 3/2003 | Lizardi .............. | A61B 17/0401 606/232 |
| 7,285,124 | B2 * | 10/2007 | Foerster ............. | A61B 17/0469 606/139 |
| 7,717,929 | B2 * | 5/2010 | Fallman ............. | A61B 17/0057 606/158 |

(Continued)

*Primary Examiner* — Eric S Gibson
*Assistant Examiner* — Marcela I Shirsat
(74) *Attorney, Agent, or Firm* — Schwegman Lundberg & Woessner, P.A.

(57) ABSTRACT

A device for securing tissue or bone. The device includes a self-locking construct, which includes first and second adjustable loops. The first adjustable loop includes a loop passage portion through which a first portion of the self-locking construct extends. The second adjustable loop extends through a sleeve defined by the self-locking construct. The self-locking construct is configured such that moving the second adjustable loop away from the first loop closes the first adjustable loop, and pulling the first portion further through the loop passage portion closes the second adjustable loop.

17 Claims, 9 Drawing Sheets

(56) References Cited

U.S. PATENT DOCUMENTS

| | | | | |
|---|---|---|---|---|
| D661,175 S | * | 6/2012 | Dahl | D8/349 |
| 8,590,116 B2 | * | 11/2013 | Dahl | D07B 1/18 |
| | | | | 24/300 |
| 9,192,373 B2 | * | 11/2015 | Sengun | A61B 17/06166 |
| 2005/0261710 A1 | * | 11/2005 | Sakamoto | A61B 17/0401 |
| | | | | 606/139 |
| 2008/0082128 A1 | * | 4/2008 | Stone | A61B 17/0401 |
| | | | | 606/232 |
| 2009/0082805 A1 | * | 3/2009 | Kaiser | A61B 17/0401 |
| | | | | 606/228 |
| 2011/0098727 A1 | * | 4/2011 | Kaiser | A61B 17/0401 |
| | | | | 606/144 |
| 2011/0208240 A1 | * | 8/2011 | Stone | A61B 17/0401 |
| | | | | 606/232 |
| 2012/0059417 A1 | * | 3/2012 | Norton | A61B 17/0401 |
| | | | | 606/232 |
| 2015/0173754 A1 | * | 6/2015 | Norton | A61B 17/0401 |
| | | | | 606/228 |

* cited by examiner though the
ADJUSTABLE LOOP CONSTRUCTS AND TECHNIQUES

FIELD

The present disclosure relates to adjustable loop constructs and techniques for use of adjustable loop constructs.

BACKGROUND

This section provides background information related to the present disclosure, which is not necessarily prior art.

Arthroscopic procedures often include sutures and anchors to secure soft tissue to bone, secure bone pieces together, and to secure separated portions of soft tissue together. Despite their widespread use, sutures and suture anchors, as well as methods for their use, can be improved. For example, tying sutures into knots may be very time consuming and difficult to perform, particularly inside the joint space. As a result, the cost of the procedure may increase and the capacity of the surgeon may be limited. Furthermore, the strength of the repair may be limited by the strength of the knot. The methods and apparatuses disclosed herein address these issues and numerous others.

SUMMARY

This section provides a general summary of the disclosure, and is not a comprehensive disclosure of its full scope or all of its features.

The present teachings provide for a device for securing tissue or bone. The device includes a self-locking construct, which includes first and second adjustable loops. The first adjustable loop includes a loop passage portion through which a first portion of the self-locking construct extends. The second adjustable loop extends through a sleeve defined by the self-locking construct. The self-locking construct is configured such that moving the second adjustable loop away from the first loop closes the first adjustable loop, and pulling the first portion further through the loop passage portion closes the second adjustable loop.

The present teachings further provide for a device for securing tissue or bone including a flexible self-locking construct. The flexible self-locking construct includes first and second adjustable loops. The first adjustable loop includes a loop body defining a loop passage portion through which a first portion of the construct extends. The second adjustable loop extends through a sleeve defined by the construct. The loop body and the first portion are both adjacent to, and transition to, the second adjustable loop. The flexible self-locking construct is configured such that moving the second loop away from the first adjustable loop closes the first adjustable loop, and pulling the first portion further through the loop passage portion closes the second adjustable loop.

The present teachings further provide for a method for securing tissue or coupling bone portions together. The method includes mating the tissue or bone portions with a flexible self-locking construct including a first adjustable loop and a second adjustable loop by placing the second adjustable loop in contact with the tissue or bone portions; and tensioning the tissue or drawing the bone portions together by pulling a portion of the construct through a loop passage portion defined by a body of the construct, the body partially defining the first adjustable loop.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
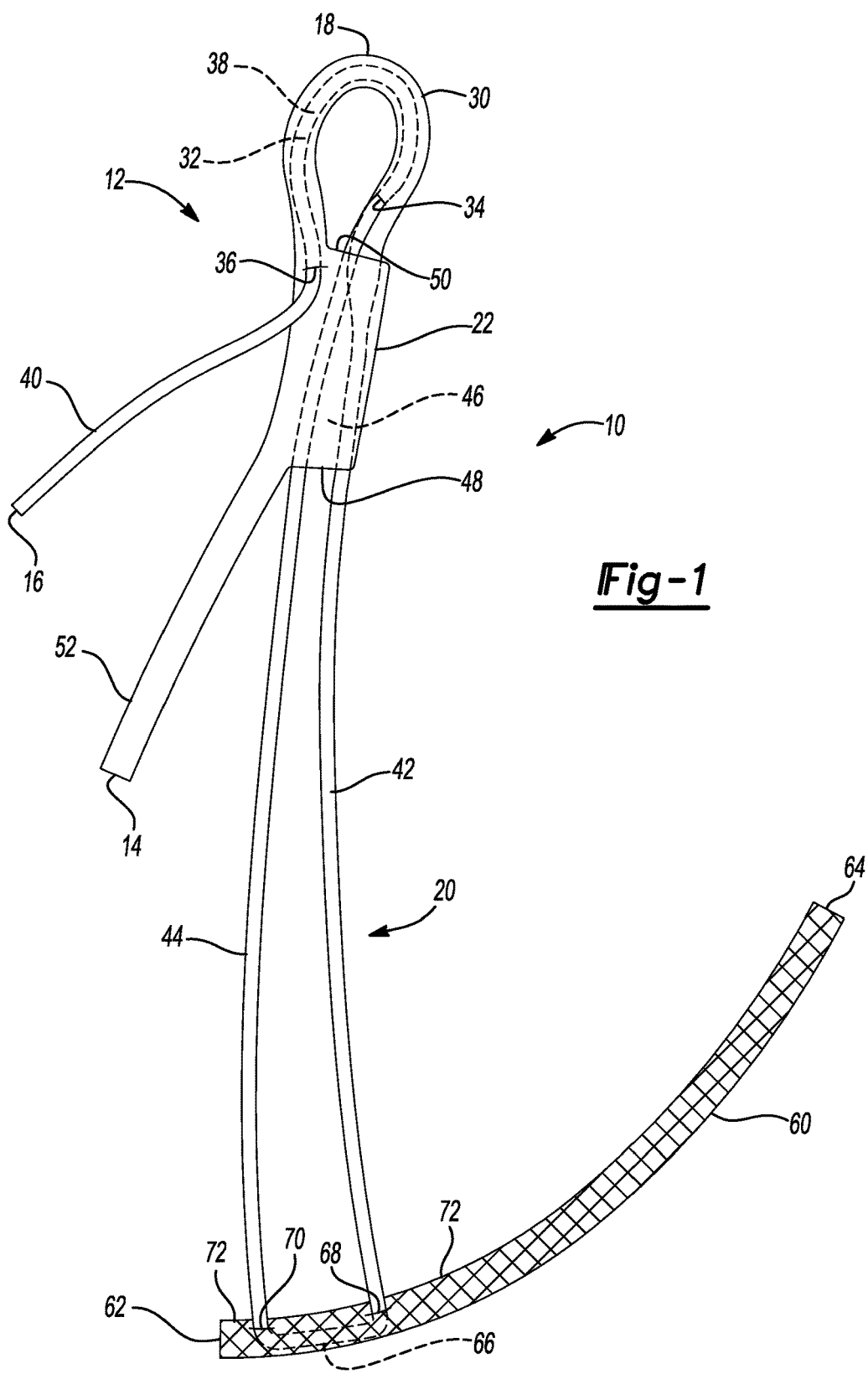
FIG. 1 illustrates a securing device according to the present teachings for securing tissue or bone.

With initial reference to FIG. 1, a securing device according to the present teachings is generally illustrated at reference numeral 10. The securing device 10 can be used, for example, to secure any suitable tissue or bone at a desired position, or to secure two tissue or two bone portions relative to one another. For example, and as further described herein, the securing device 10 can be used to secure two separated portions of a sternum, secure a bone-tendon-bone graft in a femur, or to secure tissue at a desired location.

The securing device 10 includes a self-locking construct 12, which can be made of any suitable material, such as a flexible material including suture. When the construct 12 is made of suture, any suitable suture can be used. For example, a braided hollow-core suture can be used. Any suitable braided suture can be used, such as any of the braided sutures disclosed in U.S. patent application Ser. No. 12/915,962 titled Method and Apparatus for Securing Soft Tissue to Bone, which was filed on Oct. 29, 2010, published as Publication No. 2011/0098727 on Apr. 28, 2011, and is assigned to Biomet Sports Medicine, LLC. Although the construct 12 can be made of any suitable material in addition to suture, the construct 12 will generally be described herein as a suture construct.

The suture construct 12 generally includes a first end 14 and a second end 16. The suture construct 12 is generally a unitary, one piece structure extending between the first end 14 and the second end 16. The suture construct 12 includes an outer wall extending between the first end 14 and the second end 16, which defines a passage extending from the first end 14 to the second end 16. The passage need not completely extend between the first end 14 and the second end 16, and thus may extend at one or more locations across any suitable distance between the first end 14 and the second end 16.

The suture construct 12 includes a first loop 18 and a second loop 20. One or both of the first loop 18 and the second loop 20 can be adjustable. Generally proximate to a transition area of the suture construct 12 between the first loop 18 and the second loop 20 is a sleeve or first passage portion 22, through which the second loop 20 extends, as described herein. The sleeve or first passage portion 22 can be self-locking as described herein.

The first loop 18 generally includes a loop body 30, which defines a loop passage portion or a second passage portion 32 extending between a first aperture or opening 34 in the suture construct 12 and a second aperture or opening 36 in the suture construct 12. The first aperture or opening 34 and the second aperture or opening 36 are each generally apertures at opposite ends of the loop passage portion or second passage portion 32, which extends through a sidewall of the suture construct 12 between woven fibers of the suture construct 12.

As illustrated in FIG. 1 for example, the first loop 18 can be defined by the loop body 30 and a portion of the sleeve 22. A first portion 38 of the suture construct 12 extends through the loop passage portion 32. The first portion 38 extends out from within the second aperture 36, where the suture construct 12 generally transitions to a zip strand 40. The zip strand 40 generally includes a portion of the suture construct 12 between the second end 16 and the second aperture 36. As described in further detail herein, pulling the zip strand 40 closes, or makes smaller, the second loop 20 in a self-locking manner.

Extending out from within the sleeve 22 opposite to the first loop 18 is a second portion 42 and a third portion 44 of the suture construct 12. From the first aperture 34, the loop body 30 generally transitions to the second portion 42 and extends through a sleeve passage portion 46 defined by the sleeve 22. The first portion 38 extends out from within the loop passage portion 32 at the first aperture 34, where the first portion 38 generally transitions to the third portion 44. The second portion 42 and the third portion 44 define the second loop 20, and transition together at a distal end of the second loop 20 furthest from the sleeve 22. The sleeve 22 generally includes a first sleeve opening 48 and a second sleeve opening 50 at opposite ends of the sleeve passage portion 46. The second portion 42 and the third portion 44 extend beyond the first sleeve opening 48 to define the second loop 20. The second sleeve opening 50 is proximate to the first loop 18. The sleeve openings 48 and 50 are generally apertures of one or more passages through a sidewall of the suture construct 12 between woven fibers of the suture construct 12.

Extending from the sleeve 22, such as proximate to the first sleeve opening 48, is a back-tension strand 52 of the suture construct 12. The back-tension strand 52 extends from the sleeve 22 to the first end 14. When the zip strand 40 is pulled to close the second loop 20, holding the back-tension strand 52 provides back-tension to the suture construct 12, which can keep the suture construct 12 from rotating about bone portions to be joined when the zip strand 40 is pulled to close the second loop 20.

As further described herein, pulling the zip strand 40 when the second loop 20 is tensioned self-locks the second loop 20. Specifically, tension at the second portion 42 will be transferred to the loop body 30, and thus will cause the loop passage portion 32 to collapse and compress onto the first portion 38 extending therethrough, thereby forming a mechanical locking interface. The first portion 38 will thus be restricted from moving through the loop passage portion 32, which will restrict the second loop 20 from reopening. The first loop 18 may also be self-locking. For example and as described herein, as the passing strand 60 and the second loop 20 are pulled through the first loop 18, the first and second portions 42 and 44 will be pulled further out from within the sleeve 22, which will cause the loop body 30 of the first loop 18 to be pulled into sleeve 22, thereby closing the first loop 18 onto the second loop 20 and increasing friction within the sleeve 22 by receiving therein the loop body 30 consisting of overlapped suture sections, which may form a mechanical locking interface with an interior of the sleeve 22.

The securing device 10 can further include the passing strand 60 coupled to the second loop 20. The passing strand 60 is an elongated strand made of any suitable material, such as braided hollow-core suture as described above. To distinguish the passing strand 60 from the suture construct 12, the passing strand 60 and the suture construct 12 can be provided with any suitable distinguishing visual features, such as different colors, different visual designs, and/or different diameters.

The passing strand 60 generally includes a first end 62 and a second end 64 opposite thereto. The passing strand 60 is an elongated member extending between the first end 62 and the second end 64. The passing strand 60 defines an internal passage or passage portion 66 at any suitable portion thereof, and along any suitable length thereof. For example, the internal passage 66 can be proximate to the first end 62. The internal passage or passage portion 66 can be part of a larger passage extending from the first end 62 to the second end 64 and defined by suture strands of the passing strand 60. The internal passage 66 defines a first opening 68 and a second opening 70. The second loop 20 extends through the internal passage 66. The second portion 42 of the second loop 20 extends through the first opening 68, and the third portion 44 extends through the second opening 70. The second and third portions 42 and 44 generally meet and transition together within the internal passage 66. The passing strand 60 includes leg or tail portions 72 proximate to the first and second openings 68 and 70 on sides thereof opposite to the internal passage 66. The passing strand 60 is optional, and as explained further herein can be replaced with other members or devices.

Figure 2:
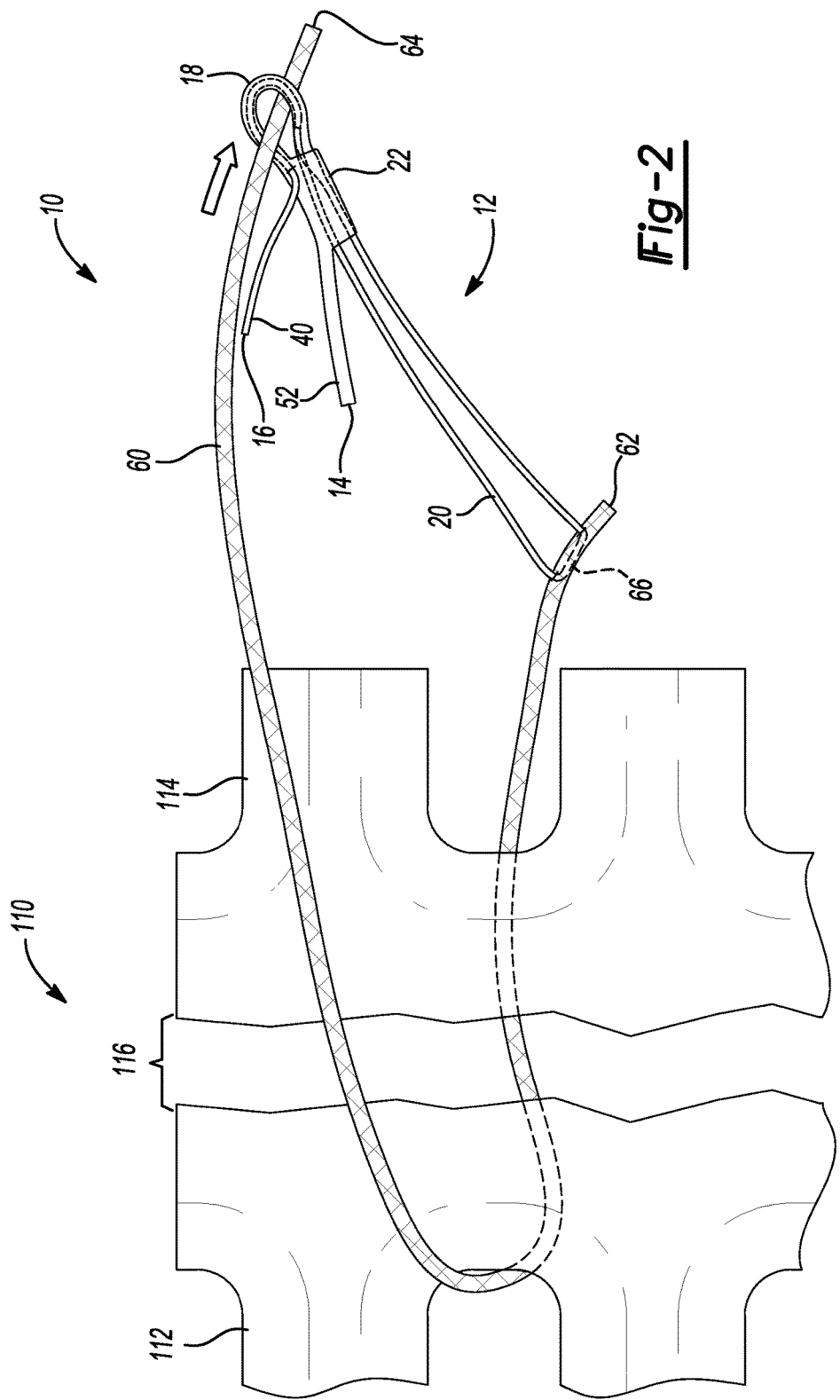
FIGS. 2-5 illustrate a method of using the securing device of FIG. 1 to secure separated bone portions together.
Figure 3:
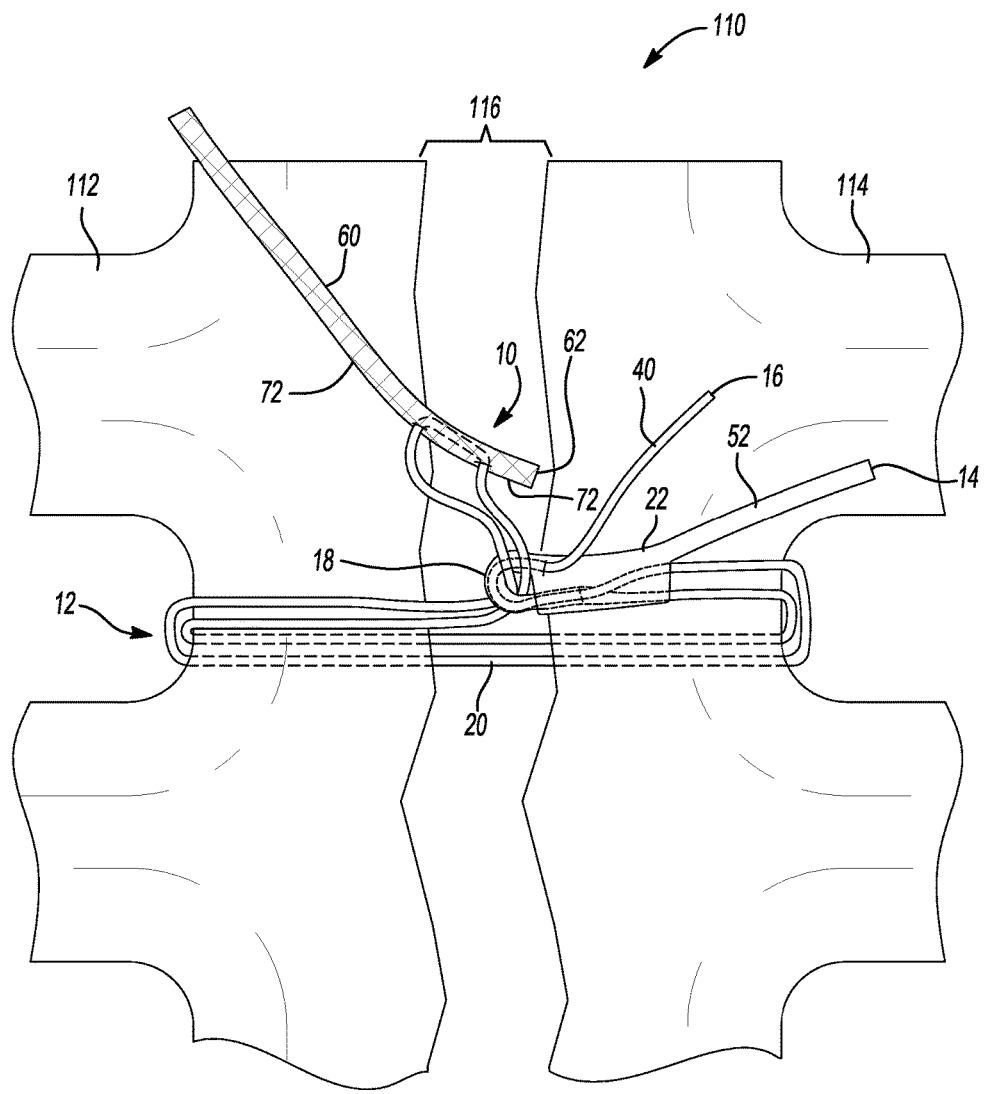

With continued reference to FIG. 1 and additional reference to FIGS. 2-5, a method of using the securing device 10 with a sternum 110 to secure together a first sternal portion 112 and a second sternal portion 114 separated by a gap 116 will now be described. As illustrated in FIG. 2, the passing strand 60 is first passed or looped around the separated first and second sternal portions 112 and 114. The second end 64 of the passing strand is then passed through the first loop 18, and pulled entirely through the first loop 18, as illustrated in FIG. 3.

Figure 4:
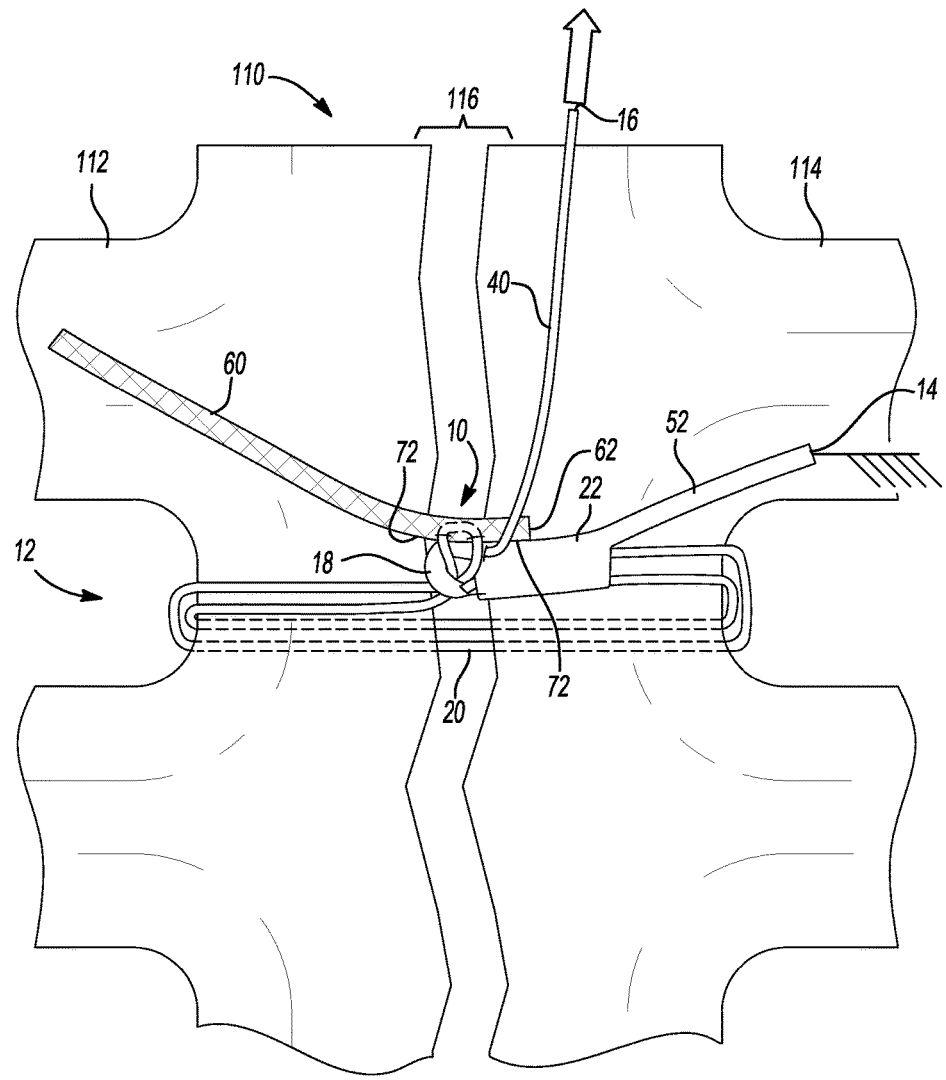

As the passing strand 60 and the second loop 20 are pulled further through the first loop 18, the first and second portions 42 and 44 will be pulled further out from within the sleeve 22, which will cause the loop body 30 to be pulled into the sleeve 22, thereby closing the first loop 18 onto the second loop 20, as illustrated in FIG. 4. Pulling the loop body 30 into the sleeve 22 may also increase friction within the sleeve 22 by receiving therein the loop body 30 consisting of overlapped suture sections, which may form a mechanical locking interface with an interior of the sleeve 22. The leg or tail portions 72 of the passing strand 60 will abut the first loop 18, and the passing strand 60 will extend across the first loop 18 thereby preventing the passing strand 60 from passing back through the first loop 18. Excess portions of the passing strand 60 can be cut away, such as with any suitable cutting device, including cutting device 130 illustrated in FIG. 5.

Figure 5:
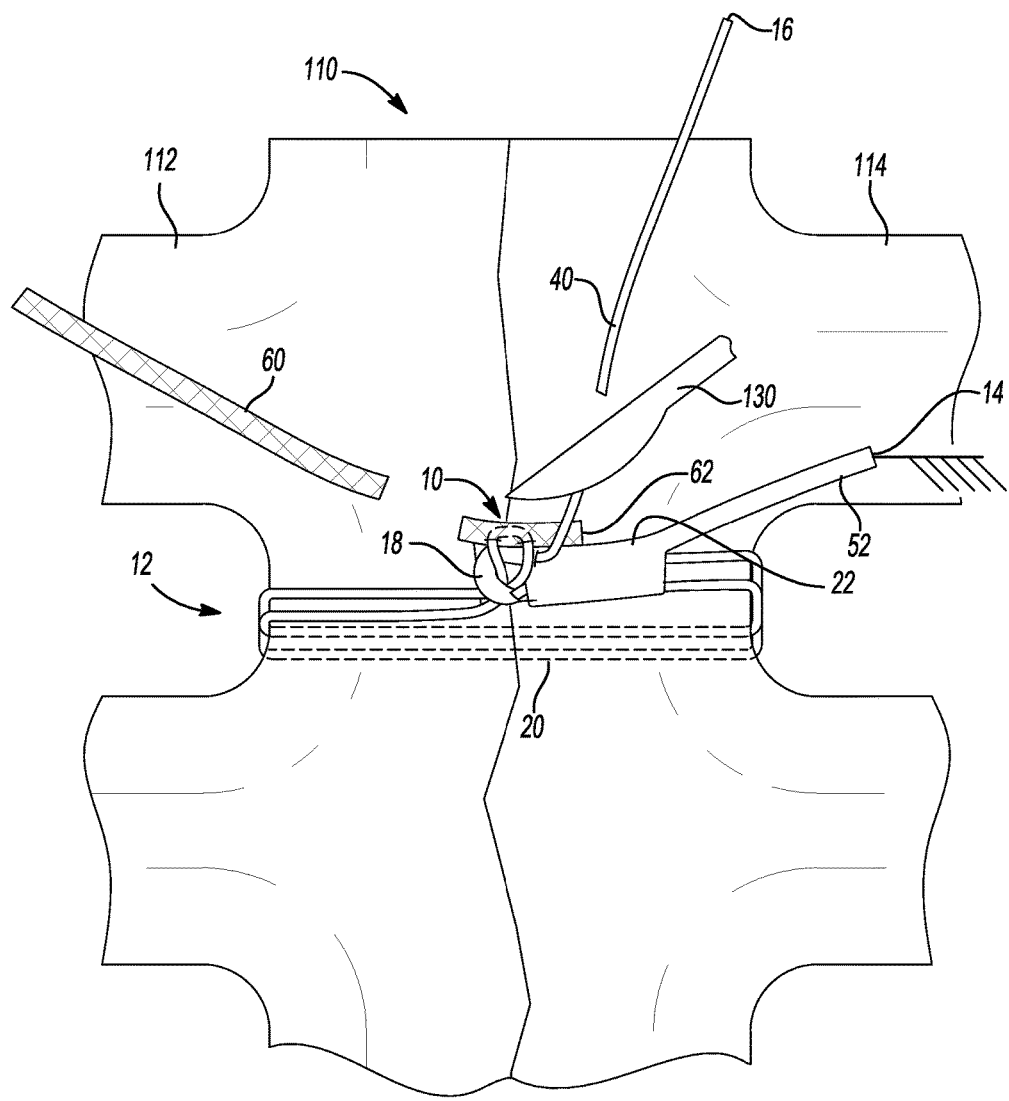

With reference to FIG. 5, after the passing strand 60 has been pulled through the loop body 30, and after the first loop 18 has closed onto the second loop 20, the second loop 20 is closed or "zipped down" by pulling the zip strand 40 at the second end 16 of the suture construct. As the zip strand 40 is pulled, the second loop 20 becomes smaller and draws the separated first sternal portion 112 and second sternal portion 114 together to close the gap 116 therebetween. To prevent the suture construct 12 from rotating or sliding around the first and second sternal portions 112 and 114 when the zip strand 40 is pulled, the back tension strand 52 at the first end 14 can be held as the zip strand 40 is pulled.

Tension applied to the second loop 20, such as by the first and second sternal portions 112 and 114, prevents the zip strand 40 from moving back through the loop passage portion 32, and thus prevents the second loop 20 from reopening. Specifically, tension at the second portion 42 will be translated to the loop body 30, and thus will cause the loop passage portion 32 to collapse and compress onto the first portion 38 extending therethrough, thereby forming a mechanical locking interface. The first portion 38 will thus be restricted from moving through the loop passage portion 32, which will restrict the second loop 20 from reopening. With reference to FIG. 5, after the second loop 20 has been tensioned, the zip strand 40 can be cut and shortened with a suitable cutting instrument, such as cutting instrument 130.

Figure 6:
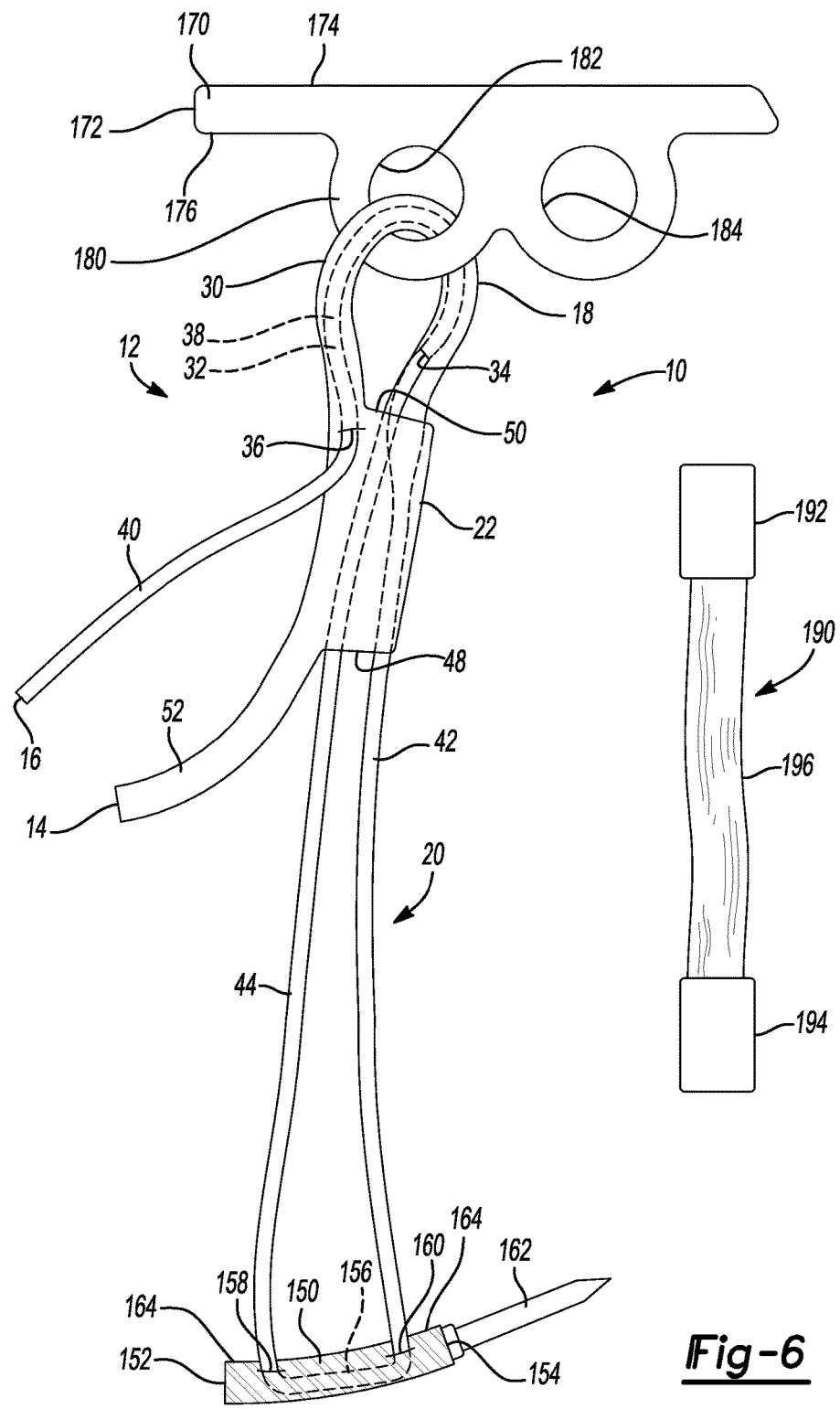
FIG. 6 illustrates the securing device of FIG. 1 modified to secure a bone-tendon-bone graft in a bone tunnel.

With reference to FIG. 6, the passing strand 60 can be replaced with an anchor 150, such as a soft or flexible anchor. The anchor 150 can be made of any suitable material, such as braided hollow-core suture, sponge or sponge-like material, perforated materials, woven/braided materials or fibers, such as, for example, polymer, polyester, polyethylene, cotton, silk, or other natural or synthetic material.

The anchor 150 generally includes a first end 152 and a second end 154. The anchor 150 is generally elongated and extends from the first end 152 to the second end 154. The anchor 150 defines an internal passage 156 extending through a portion of the anchor 150 between a first opening 158 and a second opening 160. The second loop 20 extends through the internal passage 156. Extending from the second end 154 is a needle 162. The anchor 150 further includes leg/tail portions 164 between the first end 152 and the first opening 158, as well as between the second end 154 and the second opening 160.

The device 10 of FIG. 6 further includes a fixation device 170, which can be configured to secure the device 10 at any suitable location, such as within a bone hole formed through a femur, such as during an ACL procedure. The fixation device 170 includes an elongated portion 172 with a first side 174 opposite to a second side 176. At the second side 176 is a flange 180, which defines a first aperture 182 and a second aperture 184. The first loop 18 is arranged such that is extends through the first aperture 182. The device 10 can be used to secure any suitable bone or tissue, such as a bone-tendon-bone graft 190. The graft 190 includes a first bone portion 192, a second bone portion 194, and a tendon portion 196 extending between the first and second bone portions 192 and 194. The graft 190 can be used to replace a patient's ACL.

Figure 7:
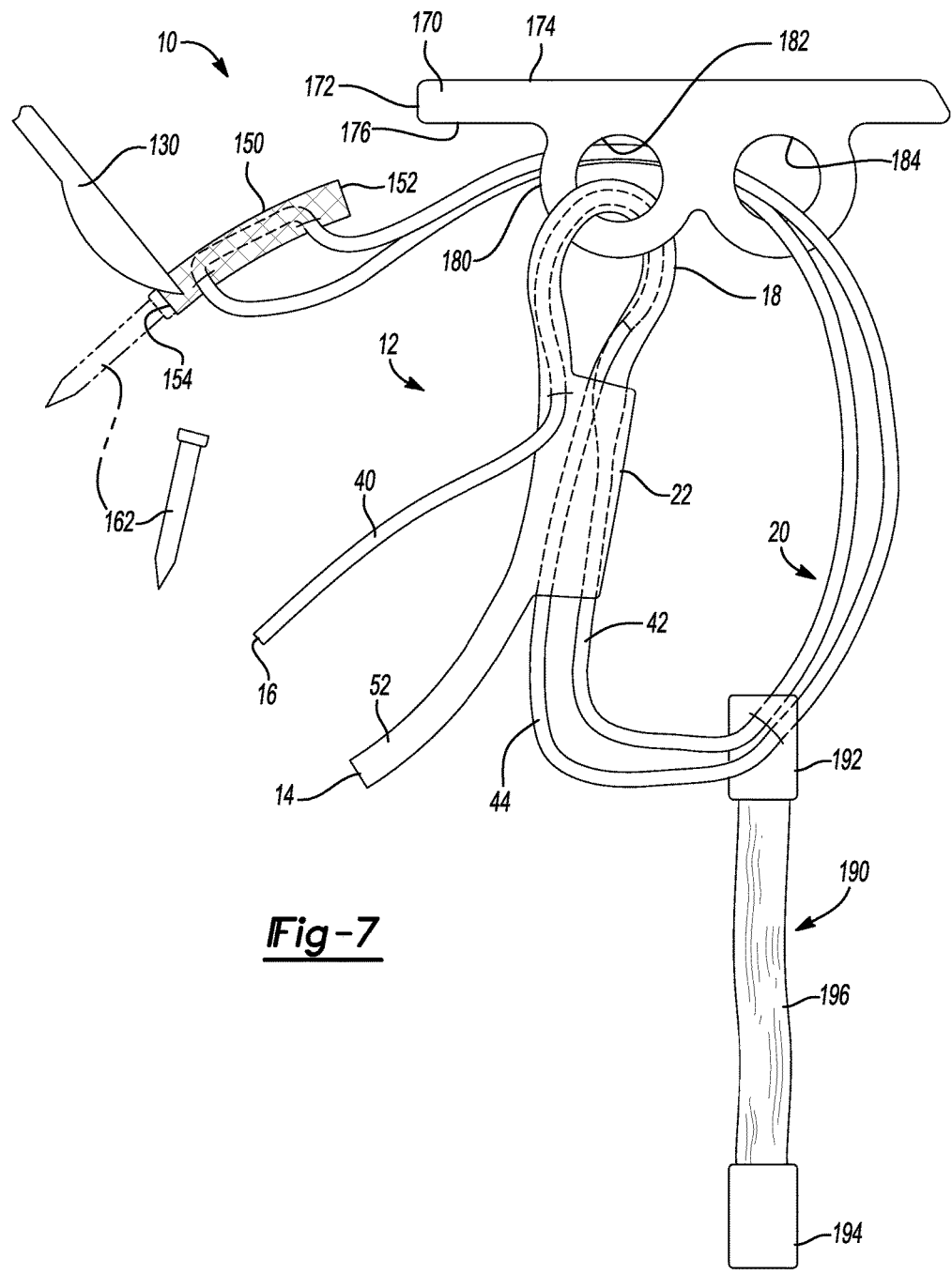
FIG. 7 illustrates use of the securing device to secure the bone-tendon-bone graft.

With continued reference to FIG. 6 and additional reference to FIG. 7, an exemplary method of using the device including the anchor 150 and the fixation device 170 will now be described. The second loop 20 is coupled to the graft 190 by passing the needle 162 and the anchor 150 through one of the first or second bone portions 192 or 194, such as the first bone portion 192 as illustrated. The needle 162 and the anchor 150 are then passed through the second aperture 184 of the fixation device 170. The anchor 150 is anchored to the flange 180 by positioning the leg/tail portions 164 of the anchor 150 against the flange 180 of the second aperture 184 after the anchor 150 has been passed through the second aperture 184. After the anchor 150 has been passed through the second aperture 184, the needle 162 can be removed from the anchor 150, such as by severing the anchor 150 proximate to the second end 154.

Figure 9:
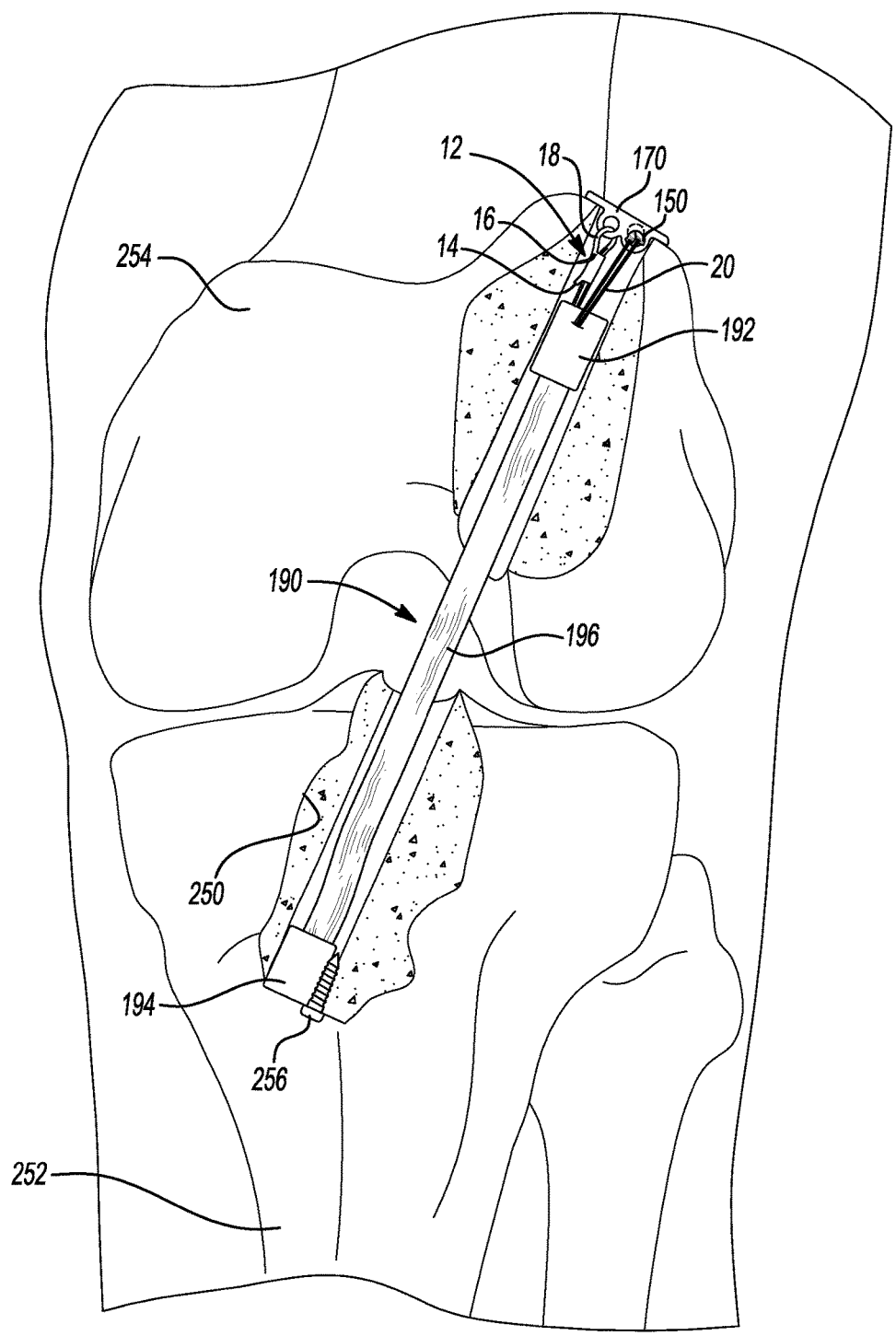
FIG. 9 illustrates the securing device of FIG. 6 in a bone tunnel to secure the bone-tendon-bone graft therein.

The graft 190 can be positioned at any suitable location, such as in a bone tunnel 250 formed through a tibia 252 and a femur 254 during ACL replacement, as illustrated in FIG. 9 for example. The fixation device 170, with the suture construct 10 and the graft 190 coupled thereto, can first be pulled into the bone tunnel 250, such as with a suture coupled to the fixation device 170, such as at the first aperture 182 or the second aperture 184. The second bone portion 194 can be anchored to the tibia 250 in any suitable manner, such as with a fastener 256. The device 10 is then pulled away from the tibia 252 to stretch the graft 190 up into the femur 254, thereby tensioning the second loop 20, which closes the first loop 18 onto the first aperture 182 of the flange 180 in accordance with the description of the first loop 18 above. To further draw the graft 190 into the femur 254 and tension both the graft 190 and the second loop 120, the zip strand 40 is pulled, which draws the fixation device 170 and the graft 190 together, and draws the fixation device 170 against the femur 254 at the bone tunnel 250 such that the second side 176 of the fixation device abuts the femur 254 and the fixation device extends across the bone tunnel 250.

Figure 8:
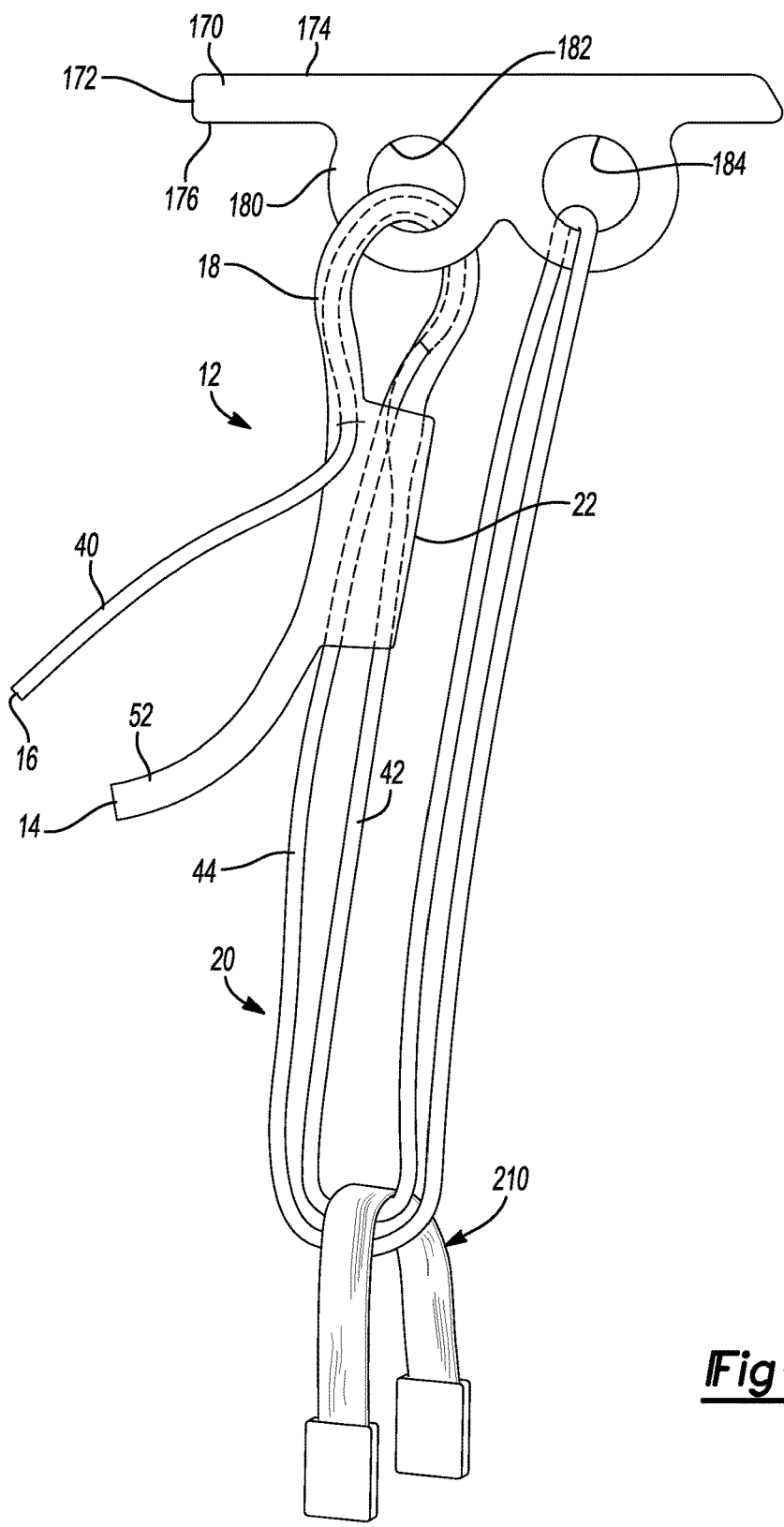
FIG. 8 illustrates the securing device of FIG. 1 modified to secure a soft tissue graft.

With additional reference to FIG. 8, the device 10 can be configured such that the second loop 20 is looped through the second aperture 184 of the fixation device 170 without the need for the anchor 150. The device 10 can be used to secure any suitable type of tissue, such as tissue 210. The tissue 210 can be secured at any suitable location, such as in the bone tunnel 250 as illustrated in FIG. 9. The tissue 210 can be folded over the second loop 20 as illustrated in FIG. 8. To tension the tissue 210 and secure it in place, the zip strand 40 can be pulled, thus drawing the tissue 210 towards the fixation device 170. The device 10 can secure the tissue 210 in the bone tunnel 250 in substantially the same manner as illustrated in FIG. 9 with respect to the graft 190. Instead of securing the tissue 210 with the fastener 256 illustrated as a screw, any other suitable fastener can be used, such as a washer block.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for securing tissue or bone, the device comprising:
   a self-locking construct including:
   a first adjustable loop including a loop passage portion through which a first portion of the self-locking construct extends to a first free end of the first portion positioned outside the loop passage portion; and
   a second adjustable loop extending through a sleeve defined by the self-locking construct;
   wherein the self-locking construct is configured such that moving the second adjustable loop away from the first loop closes the first adjustable loop, and pulling the first free end of the first portion further through the loop passage portion closes the second adjustable loop, wherein the self-locking construct is a unitary, one-piece structure, wherein at least part of the loop passage portion is positionable outside the sleeve, wherein the self-locking construct is configured such that tension in the second adjustable loop constricts the loop passage portion about the first portion, thereby forming a mechanical interface between opposing surfaces of the loop passage portion and the first portion, thereby restricting opening of the second adjustable loop and thus locking the second adjustable loop.

2. The device of claim 1, wherein the self-locking construct is a flexible suture construct.

3. The device of claim 1, wherein the first adjustable loop is partially defined by the sleeve.

4. The device of claim 1, wherein the self-locking construct further includes a back-tension strand extending from an end of the sleeve opposite to the first adjustable loop.

5. The device of claim 1, wherein the second adjustable loop includes a second portion of the self-locking construct extending out from within the sleeve and a third portion of the self-locking construct extending out from within the sleeve, and wherein said moving includes pulling either or both of the second portion and the third portion of the self-locking construct further through the sleeve away from the first adjustable loop.

6. The device of claim 1, wherein the device further comprises a passing strand coupled to the second adjustable loop configured to pass the second adjustable loop through or around tissue or bone.

7. The device of claim 6, wherein the self-locking construct is configured such that the first adjustable loop closes upon passing the passing strand through the first adjustable loop and pulling the second adjustable loop through the first adjustable loop.

8. The device of claim 1, wherein the device further comprises a soft anchor coupled to the second adjustable loop and a needle extending from the soft anchor.

9. The device of claim 1, further comprising a fixation device, wherein the first adjustable loop is coupled to the fixation device.

10. The device of claim 9, wherein the second adjustable loop is configured to be coupled to the fixation device with an anchor.

11. The device of claim 9, wherein the second adjustable loop is coupled to the fixation device.

12. A device for securing tissue or bone, the device comprising:

a flexible self-locking construct including:

a first adjustable loop including a loop body defining a loop passage portion through which a first portion of the self-locking construct extends; and a second adjustable loop extending through a sleeve defined by the self-locking construct, the loop body and the first portion are both adjacent to, and transition into, the second adjustable loop, the second adjustable loop including a second portion of the self-locking construct that extends out from within the sleeve and a third portion of the self-locking construct that extends out from within the sleeve, wherein the flexible self-locking construct is configured such that: (i) pulling only the second portion of the self-locking construct further through the sleeve away from the first adjustable loop closes the first adjustable loop; (ii) pulling only the third portion of the self-locking construct further through the sleeve away from the first adjustable loop closes the first adjustable loop; and (iii) pulling the second portion and the third portion of the self-locking construct further through the sleeve away from the first adjustable loop closes the first adjustable loop, and wherein the flexible self-locking construct is configured such that pulling the first portion further through the loop passage portion closes the second adjustable loop, wherein the flexible self-locking construct is a unitary, one-piece structure.

13. The device of claim 12, wherein the self-locking construct is configured such that tension in the second adjustable loop constricts the loop passage portion about the first portion, thereby forming a mechanical interface between opposing surfaces of the loop passage portion and the first portion, thereby restricting opening of the second adjustable loop and thus locking the second adjustable loop.

14. The device of claim 12, wherein the second adjustable loop is coupled to one of a passing strand, a flexible anchor, or a fixation device.

15. The device of claim 12, the flexible self-locking construct further comprising a fixation device defining a first aperture and a second aperture, wherein the first adjustable loop extends through the first aperture and the second adjustable loop extends through the second aperture or is configured to extend through the second aperture.

16. The device of claim 12, wherein the first adjustable loop is partially defined by the sleeve.

17. The device of claim 12, wherein at least part of the loop passage portion is positionable outside the sleeve.

* * * * *